(12) United States Patent
Funabiki et al.

(10) Patent No.: US 7,030,280 B2
(45) Date of Patent: Apr. 18, 2006

(54) PROCESS FOR PRODUCING OPTICALLY ACTIVE β-TRIFLUOROMETHYL-β-HYDROXYCARBONYL COMPOUND

(75) Inventors: Kazumasa Funabiki, Gifu (JP); Hitoshi Yamamoto, Gifu (JP); Masashi Nagamori, Gifu (JP); Masaki Matsui, Gifu (JP)

(73) Assignee: Central Glass Company, Limited, Tokyo (JP)

( * ) Notice: Subject to any disclaimer, the term of this patent is extended or adjusted under 35 U.S.C. 154(b) by 0 days.

(21) Appl. No.: 10/923,788

(22) Filed: Aug. 24, 2004

(65) Prior Publication Data

US 2005/0119507 A1    Jun. 2, 2005

(30) Foreign Application Priority Data

Dec. 2, 2003    (JP) ............................. 2003-403268

(51) Int. Cl.
 C07C 45/70    (2006.01)
(52) U.S. Cl. ...................... 568/388; 568/391; 568/393; 568/394; 568/403
(58) Field of Classification Search ................ 568/388, 568/391, 393, 394, 403
See application file for complete search history.

(56) References Cited

U.S. PATENT DOCUMENTS 6,639,100 B1 * 10/2003 Ishii et al. .................. 560/227

FOREIGN PATENT DOCUMENTS

JP    2001-226308    8/2001

OTHER PUBLICATIONS

Kitazume et al. Synthesis of fluorinated materials catalyzed by proline or antibody 38C2 in ionic liquid. Journal of Fluorine Chemistry. 2003, vol. 121, p 205-212.*
Itoh et al. Dipole Interaction-Controlled Stereoselectivity in Aldol Reaction of alpha-CF3 Enolate with Fluoral. Organic Letters. 2003, vol. 5 (25) p 4807-4809.*
Forni, Arrigo et al.: "Stereochemical Control in Yeast Reduction of Fluorinated β-Diketones", Tetrahedron, England, 1994, vol. 50, No. 41, pp. 11995-12000.
Lin, Jenq Tain et al.: "A Microbially Based Approach for the Preparation of Chiral Molecules Possessing the Trifluoromethyl Group", Journal of Organic Chemistry, USA, 1987, vol. 52, No. 15, pp. 3211-3217.
Ishii, Akihiro et al.: "Asymmetric Catalytic Friedel-Crafts Reaction of Silyl Enol Ethers with Fluoral: A Possible Mechanism of the Mukaiyama-Aldol Reactions", Organic Letters, 1999, vol. 1, No. 12, pp. 2013-2016.
Ishii, Akihiro et al.: "Asymmetric Friedel-Crafts reactions of vinyl ethers with fluoral catalyzed by chiral binaphthol-derived titanium catalysts", Journal of Fluorine Chemistry, Netherlands, 1999, vol. 97, pp. 51-55.
Mikami, Koichi et al.: "Asymmetric Catalysis of Carbonyl-Ene and Aldol Reactions with Fluoral by Chiral Binaphthol-Derived Titanium Complex", Tetrahedron, England, 1996. vol. 52, No. 1, pp. 85-98.
List, Benjamin et al.: "Proline-Catalyzed Direct Asymmetric Aldol Reactions", Journal of American Chemical Society, USA, 2000, vol. 122, No. 10, pp. 2395-2396.

* cited by examiner

Primary Examiner—Sikarl A. Witherspoon
(74) Attorney, Agent, or Firm—Young & Thompson

(57) ABSTRACT

The present invention provides a process for producing an optically active β-trifluoromethyl-β-hydroxycarbonyl compound represented by formula (3):

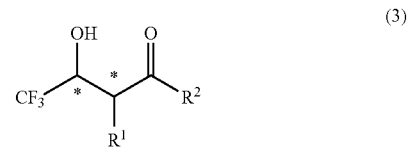

(3)

comprising a step of reacting a fluoral equivalent represented by formula (1):

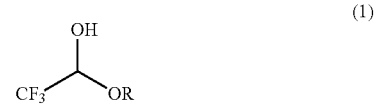

(1)

with a carbonyl compound represented by formula (2):

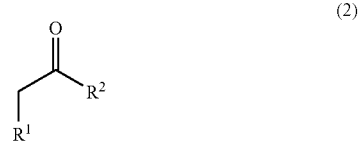

(2)

in the presence of an optically active amino acid or a derivative thereof.

20 Claims, No Drawings

PROCESS FOR PRODUCING OPTICALLY ACTIVE β-TRIFLUOROMETHYL-β-HYDROXYCARBONYL COMPOUND

FIELD OF THE INVENTION

The present invention relates to a process for producing an optically active β-trifluoromethyl-β-hydroxycarbonyl compound which is an important intermediate for medicaments and agricultural chemicals.

BACKGROUND OF THE INVENTION

The optically active β-trifluoromethyl-β-hydroxycarbonyl compound which is an objective compound of the invention is an important intermediate for medicaments and agricultural chemicals.

As processes for producing an optically active β-trifluoromethyl-β-hydroxycarbonyl compound, biological methods and chemical methods have been reported.

As the biological methods, there are known (1) a process of asymmetric reduction of a trifluoromethyl ketone compound by bread yeast (see Non-Patent Document 1) and (2) a process of optical resolution of a racemic derivative by an enzyme (see Non-Patent Document 2).

Moreover, as the chemical methods, there are known (3) a process of reacting fluoral gas with various nucleophiles in the presence of an asymmetric catalyst comprising an asymmetric ligand and a transition metal complex (see Non-Patent Documents 3, 4 and 5) and (4) a process of reacting fluoral ethyl hemiacetal with a chiral imine (see Patent Document 1).

On the other hand, a process of reacting various aldehydes with acetone in the presence of optically active proline has been already reported (see Non-Patent Document 6), but there has been no report on an example of using a hydrate (geminal-diol) or hemiacetal of an aldehyde, both of which are stable as electrophiles, especially a hydrate or hemiacetal of fluoral.

Patent Document 1: JP 2001-226308 A

Non-Patent Document 1: Tetrahedron, (England), 1994, Vol. 50, pp. 11995–20000

Non-Patent Document 2: Journal of Organic Chemistry, (USA), 1987, Vol. 52, pp. 3211–3217

Non-Patent Document 3: Organic Letters, (USA), 1999, Vol. 1, pp. 2013–2016

Non-Patent Document 4: Journal of Fluorine Chemistry, (Netherlands), 1999, Vol. 97, pp. 51–55

Non-Patent Document 5: Tetrahedron, (England), 1996, Vol. 52, pp. 85–98

Non-Patent Document 6: Journal of American Chemical Society, (USA), 2000, Vol. 122, pp. 2395–2396

In the processes described in Non-Patent Documents 1 and 2, it is necessary to construct the carbon skeleton beforehand because the processes comprise asymmetric reduction or optical resolution. In the latter case, yields have not ever exceeded 50%.

The processes described in Non-Patent Documents 3, 4 and 5 are effective since construction of the carbon skeleton and asymmetric induction can be effected simultaneously in the presence of a catalytic amount of the asymmetric catalyst. However, the processes are not satisfactory as industrial production processes since the asymmetric catalyst used therein is relatively expensive and the processes use fluoral gas which is considerably liable to polymerize.

On the other hand, the process described in Patent Document 1 is suitable as an industrial production process since stable ethyl hemiacetal of fluoral can be employed. However, the process requires an equivalent amount of a relatively expensive chiral auxiliary group and also it involves a vexatious step of synthesizing a chiral amine beforehand.

Thus, it is strongly desired to develop a process capable of producing an optically active β-trifluoromethyl-β-hydroxycarbonyl compound, which is industrially applicable.

SUMMARY OF THE INVENTION

An object of the invention is to provide an industrial process for producing an optically active β-trifluoromethyl-β-hydroxycarbonyl compound which is an important intermediate for medicaments and agricultural chemicals.

Other objects and effects of the invention will become apparent from the following description.

The present inventors have found that an asymmetric aldol reaction of stable hydrate or hemiacetal of fluoral with a carbonyl compound satisfactorily proceeds only by allowing a catalytic amount or equivalent amount of a very inexpensive optically active amino acid or derivative thereof to be present in the reaction system and thereby an optically active β-trifluoromethyl-β-hydroxycarbonyl compound is obtained.

The production process of the invention is a noteworthy process which includes characteristics that (1) construction of the carbon skeleton and asymmetric induction can be achieved simultaneously, (2) the asymmetric catalyst to be used herein is very inexpensive, (3) the reaction proceeds with a relatively high asymmetric induction even when the asymmetric catalyst is used in a catalytic amount, and (4) stable hydrate or hemiacetal of fluoral can be employed, and which solves all the problems in the conventional techniques. Moreover, it is another reason for suitableness of the process as an industrial process that the optically active amino acid or derivative thereof used as the asymmetric catalyst can be recovered in a high yield by an extremely simple operation, such as filtration of the reaction mixture after completion of the reaction.

As motioned above, the inventors have found a novel process for producing an optically active β-trifluoromethyl-β-hydroxycarbonyl compound and thus have completed the invention.

Specifically, the present invention provides the following processes.

1) A process for producing an optically active β-trifluoromethyl-β-hydroxycarbonyl compound represented by formula (3):

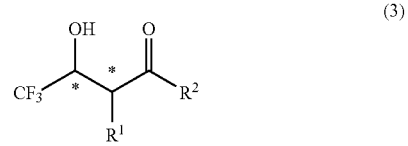

wherein $R^1$ represents a hydrogen atom, a lower alkyl group having 1 to 4 carbon atoms or a hydroxyl group, $R^2$ represents a hydrogen atom, a lower alkyl group having 1 to 4 carbon atoms or an aryl group, or $R^1$ and $R^2$ may be covalently bonded to form a cyclic ketone, and the symbol * represents an asymmetric carbon, the process comprising a step of reacting a fluoral equivalent represented by formula (1):

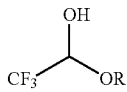

(1)

wherein R represents a hydrogen atom, a lower alkyl group having 1 to 4 carbon atoms or a lower haloalkyl group having 1 to 4 carbon atoms, with a carbonyl compound represented by formula (2):

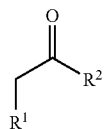

(2)

wherein $R^1$ and $R^2$ each have the same meaning as those defined in formula (3), in the presence of an optically active amino acid or a derivative thereof.

2) The process according to item 1) above, wherein the optically active amino acid is R(d)- or S(1)-proline.

3) The process according to item 1) above, wherein the fluoral equivalent represented by formula (1) is a fluoral equivalent of formula (4):

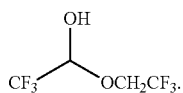

(4)

4) The process according to item 2),
wherein the fluoral equivalent of formula (1) is represented by formula (5):

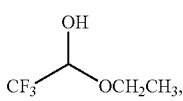

(5)

wherein the carbonyl compound of formula (2) is represented by formula (6):

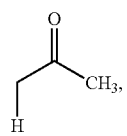

(6)

and
wherein the optically active β-trifluoromethyl-β-hydroxycarbonyl compound of formula (3) is represented by formula (7):

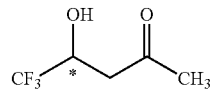

(7)

wherein the symbol * represents an asymmetric carbon.

Since the present process exhibits a high selectivity and hardly produces impurities difficult to separate as by-products, it is an extremely effective process for industrially producing an optically active β-trifluoromethyl-β-hydroxycarbonyl compound.

DETAILED DESCRIPTION OF THE INVENTION

The process for producing an optically active β-trifluoromethyl-β-hydroxycarbonyl compound according to the invention is described in more detail below.

The group R in the fluoral equivalent represented by formula (1) includes, for example, a hydrogen atom, a methyl group, an ethyl group, an n-propyl group, an i-propyl group, a cyclopropyl group, an n-butyl group, a sec-butyl group, an i-butyl group, a t-butyl group, a 2,2,2-trifluoroethyl group, a 2,2,2-trichloroethyl group, a 1,1,1,3,3,3-hexafluoro-2-propyl group, and a perfluoro-t-butyl group. Of these, preferred are a hydrogen atom, a methyl group, an ethyl group, an n-propyl group, an n-butyl group, a 2,2,2-trifluoroethyl group, a 2,2,2-trichloroethyl group and a 1,1,1,3,3,3-hexafluoro-2 -propyl group, and particularly preferred are a hydrogen atom, an ethyl group and a 2,2,2-trifluoroethyl group.

Of the fluoral equivalents represented by formula (1), the hydrate and ethyl hemiacetal are commercially available. The other hemiacetals can be synthesized by adding the hydrate or ethyl hemiacetal dropwise to concentrated sulfuric acid, phosphorus pentoxide or calcium chloride at an elevated temperature and absorbing generated fluoral gas into a corresponding lower alcohol or lower haloalcohol, followed by purification by distillation, as needed.

The group $R^1$ in the carbonyl compound represented by formula (2) includes a hydrogen atom, a methyl group, an ethyl group, an n-propyl group, an i-propyl group, a cyclopropyl group, an n-butyl group, a sec-butyl group, an i-butyl group, a t-butyl group, and a hydroxyl group.

The group $R^2$ in the carbonyl compound represented by formula (2) includes, for example, a hydrogen atom, a methyl group, an ethyl group, an n-propyl group, an i-propyl group, a cyclopropyl group, an n-butyl group, a sec-butyl group, an i-butyl group, a t-butyl group, a phenyl group, a phenyl group substituted with a lower alkyl group having 1 to 4 carbon atoms, a phenyl group substituted with a lower haloalkyl group having 1 to 4 carbon atoms, a phenyl group substituted with a lower alkoxy group having 1 to 4 carbon atoms, a naphthyl group, a naphthyl group substituted with a lower alkyl group having 1 to 4 carbon atoms, a naphthyl group substituted with a lower haloalkyl group having 1 to 4 carbon atoms, and a naphthyl group substituted with a lower alkoxy group having 1 to 4 carbon atoms.

Specific examples of the carbonyl compound represented by formula (2) include, for example, acetone, 3-pentanone, 1-hydroxyacetone, acetophenone, and cyclohexanone.

The cyclic ketone which is formed by covalently bonding $R^1$ and $R^2$ in the carbonyl compound represented by formula (2) includes, for example, cyclopropanone, cyclobutanone, cyclopentanone, cyclohexanone, cycloheptanone, cyclooctanone, 1-indanone, and α-tetralone.

The amount of the carbonyl compound represented by formula (2) to be used is not particularly limited but the compound may be usually used in an amount of 1 mol or more per mol of the fluoral equivalent represented by formula (1). The amount is preferably from 5 to 300 mol, and particularly preferably from 10 to 200 mol.

The optically active amino acid or derivative thereof includes, for example, alanine, cysteine, serine, threonine, methionine, valine, leucine, isoleucine, asparagine, glutamine, 2-azetidinecarboxylic acid, proline, phenylglycine, phenylalanine, tylosine, tryptophan, aspartic acid, glutamic acid, lysine, arginine, histidine, ornithine, citrulline, creatine, phosphoserine, γ-carboxyglutamic acid, cis- or trans-4-hydroxyproline, cis- or trans-4-acetoxyproline, cis- or trans-4-t-butoxyproline, pipecolic acid, indoline-2-carboxylic acid, 2-methoxymethylpyrrolidine, and an optically active amino acid derivative represented by formula (8):

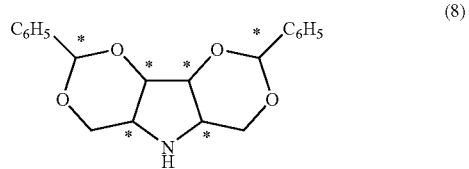

(8)

wherein the symbol * represents an asymmetric carbon and each independently has R configuration or S configuration. Of these, preferred are proline, cis- or trans-4-hydroxyproline, phenylglycine, indoline-2-carboxylic acid, 2-methoxymethylpyrrolidine, and the optically active amino acid derivative represented by formula (8), and particularly preferred is proline.

The stereochemistry of the optically active amino acid or derivative thereof may be R configuration or S configuration and, when a plurality of the asymmetric carbons are present, each independently may be R-configuration or S-configuration, and the configuration may be suitably selected depending on the stereochemistry of the aimed optically active β-trifluoromethyl-β-hydroxycarbonyl compound represented by formula (3).

The optical purity of the optically active amino acid or derivative thereof may be an enantiomer excess (e.e.) of 90% or more, and usually 95% e.e. or more is preferred and particularly 99% e.e. or more is more preferred.

There is no particular upper limit on the amount of the optically active amino acid or derivative thereof to be used. In the reaction of the invention, these compounds have a significant characteristic of being capable of serving their catalyst function not only when used in a stoichiometric amount but also when used in a catalytic amount. When economical efficiency is regarded as important, the amount is preferably 3 mol or less, particularly preferably 2 mol or less per mol of the fluoral equivalent represented by formula (1). Also, there is no particular lower limit thereon but the amount is preferably 0.01 mol or more since the reaction rate is improved, and the amount is particularly preferably 0.1 mol or more since the improvement is particularly remarkable.

The reaction solvent includes, for example, aliphatic hydrocarbons such as n-pentane, n-hexane, cyclohexane and n-heptane; aromatic hydrocarbons such as benzene, toluene, xylene and mesitylene; halogen-containing solvents such as methylene chloride, chloroform, 1,2-dichloroethane and carbon tetrachloride; ethers such as diethyl ether, tetrahydrofuran, t-butyl methyl ether and 1,4-dioxane; esters such as ethyl acetate and n-butyl acetate; alcohols such as methanol, ethanol, n-propanol and i-propanol; carboxylic acids such as acetic acid and propionic acid; amides such as hexamethylphosphoric triamide, N,N-dimethylformamide, N,N-dimethylacetamide and N-methylpyrrolidone; nitriles such as acetonitrile and propionitrile; dimethylsulfoxide, and water. Of these, preferred are n-hexane, n-heptane, benzene, toluene, methylene chloride, chloroform, tetrahydrofuran, t-butyl methyl ether, N,N-dimethylformamide, N,N-dimethylacetamide, acetonitrile, propionitrile, dimethylsulfoxide, and water. Particularly, more preferred are n-hexane, benzene, methylene chloride, chloroform, tetrahydrofuran, N,N-dimethylformamide, acetonitrile, and dimethylsulfoxide. These reaction solvents can be used singly or in combination. Alternatively, the carbonyl compound represented by formula (2) may be used in an excess amount so as to further give a role of the reaction solvent.

The amount of the reaction solvent is not particularly limited, but the solvent may be usually used in an amount of 0.1 L or more per mol of the fluoral equivalent represented by formula (1). The amount is preferably from 0.5 to 30 L and particularly preferably from 1 to 15 L.

Temperature condition for the reaction is usually from −50 to +150° C., preferably from −30 to +125° C., and particularly preferably from −10 to +100° C. Depending on the temperature condition employed, a pressure-tight reaction vessel can be used.

Reaction time is usually from 0.1 to 240 hours. However, since it varies depending on the reaction substrate, the asymmetric catalyst and the reaction conditions employed, it is preferred to trace the progress of the reaction by an analyzing means such as gas chromatography, liquid chromatography, thin-layer chromatography or NMR to determine an end point as a time point when the starting materials almost disappear.

Post-treatment is not particularly limited, but after completion of the reaction, a crude product of the aimed optically active β-trifluoromethyl-β-hydroxycarbonyl compound represented by formula (3) can be obtained by usual operations for the post-treatment, such as an extraction operation into an organic solvent, a washing operation with a saturated saline solution, and a concentrating operation under a reduced pressure. The crude product may be subjected to purification operations such as treatment with active carbon, distillation, recrystallization and/or column chromatography, as needed, to thereby obtain a product having a higher chemical purity. Alternatively, it is also effective to subject the reaction mixture after completion of the reaction directly to distillation.

The optically active amino acid or derivative thereof used as the asymmetric catalyst can be conveniently recovered in a good yield by filtrating the reaction mixture after completion of the reaction through a glass filter or the like. Referring to the condensation with acetone using an optically active proline as the asymmetric catalyst, it can be particularly effectively recovered in the case where acetone is used in an excess amount so as to act also as the solvent. The recovered asymmetric catalyst can be re-used as it is or after purified by operations such as drying, treatment with active carbon, distillation, recrystallization and/or column chromatography.

In the case where a reaction substrate wherein $R^1$ in the carbonyl compound represented by formula (2) is other than a hydrogen atom is used, two asymmetric carbons are present in the aimed optically active β-trifluoromethyl-β-hydroxycarbonyl compound represented by formula (3), and their relative stereochemistry may be syn-configuration or anti-configuration. The combination of their absolute configuration may be R-R configuration, R-S configuration, S-R configuration or S-S configuration, wherein the absolute configuration shown before the hyphen represents the stereochemistry of the β-position at which the trifluoromethyl group is present and the absolute configuration shown after the hyphen represents the stereochemistry of the α-position at which $R^1$ is present.

Since the combination of the absolute configurations at the α- and β-positions varies depending on the reaction substrate, the asymmetric catalyst and the reaction conditions, it may be suitably selected depending on the stereochemistry of the aimed optically active β-trifluoromethyl-β-hydroxycarbonyl compound represented by formula (3). In the case where a reaction substrate wherein $R^1$ is a hydrogen atom is used, only one asymmetric carbon is present in the aimed optically active β-trifluoromethyl-β-hydroxycarbonyl compound represented by formula (3) and the stereochemistry may be R configuration or S configuration.

EXAMPLES

The present invention will be illustrated in greater detail with reference to the following Examples, but the invention should not be construed as being limited thereto. As acetone, anhydrous acetone having water content of 0.005% at the maximum (manufactured by Kanto Chemical Co., Inc.) was used.

Examples 1 to 15

The results obtained in Examples 1 to 15 are summarized in Table 1. All the Examples were carried out in a similar manner. Examples 3 and 8 are shown below as representatives.

TABLE 1

![Reaction scheme: CF3-CH(OH)-OR (1, 1 mmol) + R2-CO-CH2-R1 (2, 2 ml) → (Asymmetric catalyst, Reaction solvent (8 ml)) → CF3-C*H(OH)-CH(R1)-CO-R2 (3)]

| Example | 1 | 2 | a.c.*a | Reaction solvent | Temp.*b | Reaction time | Yield of 3*c | r.y. of a.c.*d | e.e. of 3*e |
|---|---|---|---|---|---|---|---|---|---|
| 1 | 1a (R = C$_2$H$_5$) | 2a ($R^1$ = H, $R^2$ = CH$_3$) | S-(l)-proline 0.3 mmol | DMSO*f | Room temperature | 48 hours | 96% | Not conducted | 3a ($R^1$ = H, $R^2$ = CH$_3$) 3% e.e., R |
| 2 | 1a (R = C$_2$H$_5$) | 2a ($R^1$ = H, $R^2$ = CH$_3$) | S-(l)-proline 0.3 mmol | THF*g | Room temperature | 48 hours | 19% | Not conducted | 3a ($R^1$ = H, $R^2$ = CH$_3$) 37% e.e., R |
| 3 | 1a (R = C$_2$H$_5$) | 2a ($R^1$ = H, $R^2$ = CH$_3$) | S-(l)-proline 0.3 mmol | CH$_3$CN | Room temperature | 48 hours | 64% | Not conducted | 3a ($R^1$ = H, $R^2$ = CH$_3$) 42% e.e., R |
| 4 | 1a (R = C$_2$H$_5$) | 2a ($R^1$ = H, $R^2$ = CH$_3$) | S-(l)-proline 0.3 mmol | CH$_2$Cl$_2$ | Room temperature | 48 hours | 45% | Not conducted | 3a ($R^1$ = H, $R^2$ = CH$_3$) 48% e.e., R |
| 5 | 1a (R = C$_2$H$_5$) | 2a ($R^1$ = H, $R^2$ = CH$_3$) | S-(l)-proline 0.3 mmol | Benzene | Room temperature | 48 hours | 32% | Not conducted | 3a ($R^1$ = H, $R^2$ = CH$_3$) 52% e.e., R |
| 6 | 1a (R = C$_2$H$_5$) | 2a ($R^1$ = H, $R^2$ = CH$_3$) | S-(l)-proline 0.3 mmol | n-Hexane | Room temperature | 48 hours | 19% | Not conducted | 3a ($R^1$ = H, $R^2$ = CH$_3$) 46% e.e., R |
| 7 | 1a (R = C$_2$H$_5$) | 2a ($R^1$ = H, $R^2$ = CH$_3$) | S-(l)-proline 1 mmol | n-Hexane | Room temperature | 48 hours | 19% | Not conducted | 3a ($R^1$ = H, $R^2$ = CH$_3$) 50% e.e., R |
| 8 | 1a (R = C$_2$H$_5$) | 2a ($R^1$ = H, $R^2$ = CH$_3$) | S-(l)-proline 1 mmol | Acetone | Room temperature | 24 hours | 95% | 97% | 3a ($R^1$ = H, $R^2$ = CH$_3$) 37% e.e., R |

*aAsymmetric catalyst.
*bReaction temperature.
*cYield of compound 3, which is determined by $^{19}$F-NMR internal standard method (internal standard substance; CF$_3$C$_6$H$_5$).
*dRecovery yield of asymmetric catalyst. After completion of the reaction, it is recovered by filtration through a glass filter.
*eEnantiomer excess of compound 3. After p-chlorobenzoylation, it is determined by chiral HPLC (chiral column: DAICEL CHIRALCEL OD-H, mobile phase: n-hexane/i-propanol = 95/5).
*fDimethylsulfoxide.
*gTetrahydrofuran.

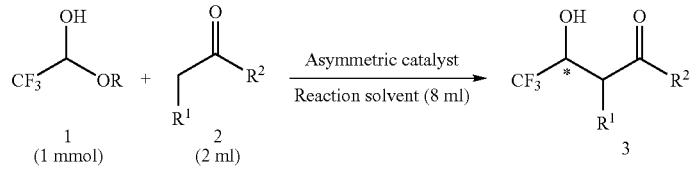

| Example | 1 | 2 | a.c.*a | Reaction solvent | Temp.*b | Reaction time | Yield of 3*c | r.y. of a.c.*d | e.e. of 3*e |
|---|---|---|---|---|---|---|---|---|---|
| 9 | 1b (R = H) | 2a ($R^1$ = H, $R^2$ = CH$_3$) | S-(l)-proline 1 mmol | Acetone | Room temperature | 24 hours | 45% | 98% | 3a ($R^1$ = H, $R^2$ = CH$_3$) 35% e.e., R |
| 10 | 1c (R = CH$_2$CF$_3$) | 2a ($R^1$ = H, $R^2$ = CH$_3$) | S-(l)-proline 1 mmol | Acetone | Room temperature | 24 hours | 96%*f | 93% | 3a ($R^1$ = H, $R^2$ = CH$_3$) 43% e.e., R |

TABLE 1-continued

| | | | | | | | | |
|---|---|---|---|---|---|---|---|---|
| 11 | 1a (R = $C_2H_5$) | 2a ($R^1$ = H, $R^2$ = $CH_3$) | S-(l)-proline 1 mmol | Acetone | Reflux | 1 hours | >99% | 95% | 3a ($R^1$ = H, $R^2$ = $CH_3$) 15% e.e., R |
| 12 | 1a (R = $C_2H_5$) | 2a ($R^1$ = H, $R^2$ = $CH_3$) | S-(l)-proline 1 mmol | Acetone | 0° C. | 96 hours | 18% | 97% | 3a ($R^1$ = H, $R^2$ = $CH_3$) 43% e.e., R |
| 13 | 1a (R = $C_2H_5$) | 2b ($R^1$ = H, $R^2$ = $C_6H_5$) | S-(l)-proline 0.5 mmol | DMSO*g | Room temperature | 8 days | 15%*f | Not conducted | 3b ($R^1$ = H, $R^2$ = $C_6H_5$) 10% e.e., R |
| 14 | 1a (R = $C_2H_5$) | 2a ($R^1$ = H, $R^2$ = $CH_3$) | Trans-4-hydroxy-S-(l)-proline 0.3 mmol | DMSO*g | Room temperature | 48 hours | 14% | Not conducted | 3a ($R^1$ = H, $R^2$ = $CH_3$) 10% e.e., R |
| 15 | 1a (R = $C_2H_5$) | 2a ($R^1$ = H, $R^2$ = $CH_3$) | S-2-methoxy-methyl-pyrrolidine 1 mmol | Acetone | Room temperature | 24 hours | 49%*h | Not conducted | 3a ($R^1$ = H, $R^2$ = $CH_3$) 15% e.e., R |

*aAsymmetric catalyst.
*bReaction temperature.
*cYield of compound 3, which is determined by $^{19}$F-NMR internal standard method (internal standard substance; $CF_3C_6H_5$).
*dRecovery yield of asymmetric catalyst. After completion of the reaction, it is recovered by filtration through a glass filter.
*eEnantiomer excess of compound 3. After p-chlorobenzoylation, it is determined by chiral HPLC (chiral column: DAICEL CHIRALCEL OD-H, mobile phase: n-hexane/i-propanol = 95/5).
*fIsolated yield by column chromatography (n-hexane/diethyl ether system).
*gDimethylsulfoxide.
*hIt is determined by $^1$H-NMR internal standard method (internal standard substance; $C_6H_5CH_2OH$).

Example 3

To an acetonitrile solution (amount of acetonitrile: 8 ml) containing 35 mg (0.3 mmol, 0.3 eq.) of S(1)-proline and 2 ml (1.6 g, 27.2 mmol, 27.2 eq.) of acetone was added 144 mg (1.0 mmol, 1 eq.) of a fluoral equivalent represented by the following formula:

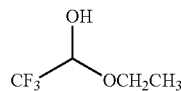

and the whole was stirred at room temperature for 48 hours. A saturated saline solution was added to the reaction mixture after completion of the reaction and the resulting mixture was extracted with diethyl ether. The recovered organic layer was washed with a saturated saline solution, dried over anhydrous sodium sulfate, and concentrated under reduced pressure.

To the residue was added 146 mg (1.0 mmol, 1.0 eq.) of α,α,α-trifluorotoluene as an internal standard substance, followed by $^{19}$F-NMR measurement. Based on relative intensity in the integration curve, the yield of the optically active β-trifluoromethyl-β-hydroxycarbonyl compound represented by the following formula:

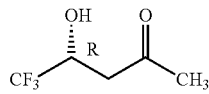

was calculated and found to be 64%. (By purifying a residue obtained in a similar manner by column chromatography (silica gel; n-hexane/diethyl ether) the optically active β-trifluoromethyl-β-hydroxycarbonyl compound represented by the above formula could be isolated in a high chemical purity. The NMR yield and isolated yield in this case were well coincident with each other. The optical purity of the isolated purified product was found to be 36% e.e. (R-isomer) when determined by chiral column analysis of its p-chlorobenzoate derivative to be mentioned below and $[\alpha]^{26}_D$ was found to be +10.7 (1.07, $CHCl_3$).)

The optical purity of the obtained optically active β-trifluoromethyl-β-hydroxycarbonyl compound was determined by chiral column analysis after its conversion into the p-chlorobenzoate derivative represented by the following formula:

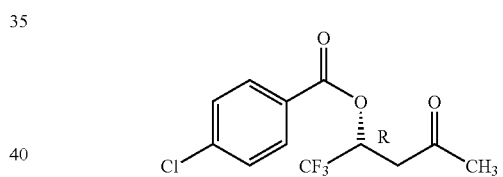

and found to be 42% e.e. (R-isomer).

Conversion into p-Chlorobenzoate Derivative and Chiral Column Analysis

To a methylene chloride solution (amount of methylene chloride: 2 ml) containing a whole amount of the resulting optically active β-trifluoromethyl-β-hydroxycarbonyl compound (0.64 mmol, 1 eq.), 130 mg (1.28 mmol, 2.0 eq.) of triethylamine and 16 mg (0.13 mmol, 0.2 eq.) of 4-dimethylaminopyridine, was added 224 mg (1.28 mmol, 2.0 eq.) of p-chlorobenzoyl chloride, and the whole was stirred at room temperature for 24 hours. A saturated sodium hydrogen carbonate aqueous solution was added to the reaction mixture after completion of the reaction and the resulting mixture was extracted with diethyl ether. The recovered organic layer was washed with a saturated sodium hydrogen carbonate aqueous solution, dried over anhydrous sodium sulfate, concentrated under reduced pressure, and vacuum-dried.

The residue was purified by column chromatography (silica gel; benzene) to obtain 74 mg (0.25 mmol) of p-chlorobenzoate derivative. The yield was 39%. One-milligram portion of the resulting p-chlorobenzoate derivative was dissolved into 1 ml of a mobile phase and then measured by high performance liquid chromatography (chiral column; DAICEL CHIRALCEL OD-H, mobile phase; n-hexane/1-propanol=95/5).

Instrumental data of the p-chlorobenzoate derivative are shown below:

Rf (silica gel; benzene): 0.30,
IR (KBr, cm$^{-1}$): 1743.9 (C=O), 1595.3 (C=O),
$^1$H-NMR (standard substance: TMS, solvent: CDCl$_3$, δ ppm): 2.23 (s, 3H), 2.96–3.11 (m, 2H), 6.05–6.09 (m, 1H), 7.42–7.44 (m, 2H), 7.96–7.98 (m, 2H),
$^{13}$C-NMR (standard substance: TMS, solvent: CDCl$_3$, δ ppm): 30.17 (s), 41.62 (s), 66.15 (q, 33.63 Hz), 123.61 (q, 280.37 Hz), 126.95 (s), 128.92 (s), 131.36 (s), 140.36 (s), 163.46 (s), 201.56 (s),
$^{19}$F-NMR (standard substance: CF$_3$CO$_2$H, solvent: CDCl$_3$, δ ppm): 0.57 (d, 6.87 Hz, 3F),
MS m/z (relative intensity): 296 (M$^+$+2, 0.8), 294 (M$^+$, 1.8), 156 (21.9), 141 (32.9), 139 (100.0), 123 (17.0), 113 (14.4), 111 (41.8),
HRMS (EI): Found: m/z, 296.0250, Calcd. for C$_{12}$H$_{10}$$^{37}$ClF$_3$O$_3$, M: 296.0271, Found: m/z, 294.0274, Calcd. for C$_{12}$H$_{10}$$^{35}$ClF$_3$O$_3$, M: 294.0271.

Example 8

To an acetone solution (amount of acetone: 10 ml, 7.9 g, 136.2 mmol, 136.2 eq.) containing 115 mg (1.0 mmol, 1.0 eq.) of S(l)-proline was added 144 mg (1.0 mmol, 1 eq.) of a fluoral equivalent represented by the following formula:

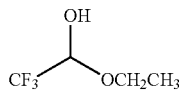

and the whole was stirred at room temperature for 24 hours. The reaction mixture after completion of the reaction was filtrated through a glass filter to recover S(l)-proline insoluble in the reaction mixture (The obtained product is taken as "product A"). Furthermore, diethyl ether was added to the filtrate to precipitate S(l)-proline dissolved in the filtrate, which was again filtrated (The obtained product is taken as "product B"). The resulting products A and B were vacuum-dried together to recover 112 mg of S(l)-proline. The recovery yield was 97%. The filtrate was concentrated under reduced pressure. To the residue was added 146 mg (1.0 mmol, 1.0 eq.) of α,α,α-trifluorotoluene as an internal standard substance, followed by $^{19}$F-NMR measurement. Based on relative intensity in the integration curve, the yield of the optically active β-trifluoromethyl-β-hydroxycarbonyl compound represented by the following formula:

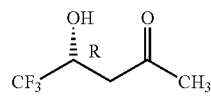

was calculated and found to be 95%.

The optical purity of the obtained optically active β-trifluoromethyl-β-hydroxycarbonyl compound was found to be 37% e.e. (R-isomer) when determined by chiral column analysis after its conversion into the p-chlorobenzoate derivative represented by the following formula:

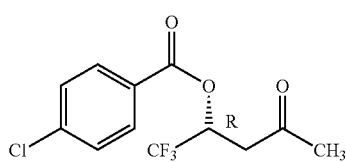

The conversion into the p-chlorobenzoate derivative and the chiral column analysis were carried out in a similar manner to Example 3.

Example 16

To a cyclopentanone solution (amount of cyclopentanone: 10 ml, 9.5 g, 113.1 mmol, 113.1 eq.) containing 35 mg (0.3 mmol, 0.3 eq.) of S(l)-proline was added 144 mg (1.0 mmol, 1 eq.) of a fluoral equivalent represented by the following formula:

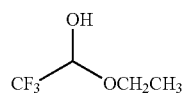

and the whole was stirred at room temperature for 48 hours. A saturated saline solution was added to the reaction mixture after completion of the reaction and the resulting mixture was extracted with diethyl ether. The recovered organic layer was washed with a saturated saline solution, dried over anhydrous sodium sulfate, and concentrated under reduced pressure.

To the residue was added 146 mg (1.0 mmol, 1.0 eq.) of α,α,α-trifluorotoluene as an internal standard substance, followed by $^{19}$F-NMR or gas chromatography measurement. Based on relative intensity in the integration curve or the area percentage, the yield (NMR yield or GC yield) of the optically active β-trifluoromethyl-β-hydroxycarbonyl compound represented by the following formula:

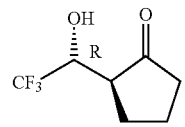

was calculated and found to be higher than 99%. By purifying the residue by column chromatography (silica gel; n-hexane/diethyl ether), the optically active β-trifluoromethyl-β-hydroxycarbonyl compound represented by the above formula could be isolated in a high chemical purity. The isolated yield was 77%. The relative stereochemistry of the isolated purified product was determined by $^{19}$F-NMR or gas chromatography and found to have a ratio of syn-configuration to anti-configuration of 8:92. The optical purity of the major product, i.e., the anti-configuration product was measured with $^{19}$F-NMR in accordance with Mosher method and found to be 97% e.e. (R-isomer at i-position).

Example 17

To a cyclohexanone solution (amount of cyclohexanone: 10 ml, 9.5 g, 96.5 mmol, 96.5 eq.) containing 35 mg (0.3 mmol, 0.3 eq.) of S(l)-proline was added 144 mg (1.0 mmol, 1 eq.) of a fluoral equivalent represented by the following formula:

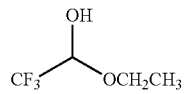

and the whole was stirred at room temperature for 48 hours. A saturated saline solution was added to the reaction mixture after completion of the reaction and the resulting mixture was extracted with diethyl ether. The recovered organic layer was washed with a saturated saline solution, dried over anhydrous sodium sulfate, and concentrated under reduced pressure.

To the residue was added 146 mg (1.0 mmol, 1.0 eq.) of α,α,α-trifluorotoluene as an internal standard substance, followed by $^{19}$F-NMR or gas chromatography measurement. Based on relative intensity in the integration curve or the area percentage, the yield (NMR yield or GC yield) of the optically active β-trifluoromethyl-β-hydroxycarbonyl compound represented by the following formula:

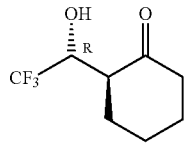

was calculated and found to be 57%. By purifying the residue by column chromatography (silica gel; n-hexane/diethyl ether), the optically active β-trifluoromethyl-β-hydroxycarbonyl compound represented by the above formula could be isolated in a high chemical purity. The isolated yield was 41%. The relative stereochemistry of the isolated purified product was determined by $^{19}$F-NMR or gas chromatography and found to have a ratio of syn-configuration to anti-configuration of 4:96. The optical purity of the major product, i.e., the anti-configuration product was measured with $^{19}$F-NMR in accordance with Mosher method and found to be higher than 98% e.e. (R-isomer at I-position).

While the present invention has been described in detail and with reference to specific examples thereof, it will be apparent to one skilled in the art that various changes and modifications can be made therein without departing from the spirit and scope thereof.

The present application is based on Japanese patent application No. 2003-403268 filed Dec. 2, 2003, the content thereof being herein incorporated by reference.

What is claimed is:

1. A process for producing an optically active β-trifluoromethyl-β-hydroxycarbonyl compound represented by formula (3):

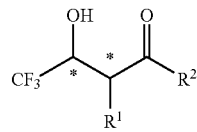

wherein $R^1$ represents a hydrogen atom, a lower alkyl group having 1 to 4 carbon atoms or a hydroxyl group, $R^2$ represents a hydrogen atom, a lower alkyl group having 1 to 4 carbon atoms or an aryl group, or $R^1$ and $R^2$ may be covalently bonded to form a cyclic ketone, and the symbol * represents an asymmetric carbon, the process comprising a step of reacting a fluoral equivalent represented by formula (1):

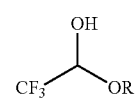

wherein R represents a hydrogen atom, a lower alkyl group having 1 to 4 carbon atoms or a lower haloalkyl group having 1 to 4 carbon atoms, with a carbonyl compound represented by formula (2):

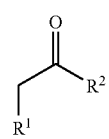

wherein $R^1$ and $R^2$ each have the same meaning as those defined in formula (3), in the presence of an optically active amino acid or a derivative thereof.

2. The process according to claim 1, wherein the group R in formula (1) is selected from the group consisting of a hydrogen atom, a methyl group, an ethyl group, an n-propyl group, an i-propyl group, a cyclopropyl group, an n-butyl group, a sec-butyl group, an i-butyl group, a t-butyl group, a 2,2,2-trifluoroethyl group, a 2,2,2-trichloroethyl group, a 1,1,1,3,3,3-hexafluoro-2-propyl group, and a perfluoro-t-butyl group.

3. The process according to claim 2, wherein the group R in formula (1) is a hydrogen atom, a methyl group, an ethyl group, an n-propyl group, an n-butyl group, a 2,2,2-trifluoroethyl group, a 2,2,2-trichloroethyl group or a 1,1,1,3,3,3-hexafluoro-2-propyl group.

4. The process according to claim 3, wherein the group R in formula (1) is a hydrogen atom, an ethyl group, or a 2,2,2-trifluoroethyl group.

5. The process according to claim 4, wherein the fluoral equivalent represented by formula (1) is a fluoral equivalent of formula (4):

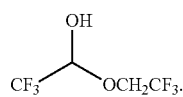
(4)

6. The process according to claim 1, wherein the group $R^1$ in formula (2) is selected from the group consisting of a hydrogen atom, a methyl group, an ethyl group, an n-propyl group, an i-propyl group, a cyclopropyl group, an n-butyl group, a sec-butyl group, an i-butyl group, a t-butyl group, and a hydroxyl group.

7. The process according to claim 1, wherein the group $R^2$ in formula (2) is selected from the group consisting of a hydrogen atom, a methyl group, an ethyl group, an n-propyl group, an i-propyl group, a cyclopropyl group, an n-butyl group, a sec-butyl group, an i-butyl group, a t-butyl group, a phenyl group, a phenyl group substituted with a lower alkyl group having 1 to 4 carbon atoms, a phenyl group substituted with a lower haloalkyl group having 1 to 4 carbon atoms, a phenyl group substituted with a lower alkoxy group having 1 to 4 carbon atoms, a naphthyl group, a naphthyl group substituted with a lower alkyl group having 1 to 4 carbon atoms, a naphthyl group substituted with a lower haloalkyl group having 1 to 4 carbon atoms, and a naphthyl group substituted with a lower alkoxy group having 1 to 4 carbon atoms.

8. The process according to claim 1, wherein the carbonyl compound of formula (2) is acetone, 3-pentanone, 1-hydroxyacetone, acetophenone, cyclopropanone, cyclobutanone, cyclopentanone, cyclohexanone, cycloheptanone, cyclooctanone, 1-indanone, or α-tetralone.

9. The process according to claim 1, wherein the carbonyl compound of formula (2) is used in an amount of 1 mol or more per mol of the fluoral equivalent represented by formula (1).

10. The process according to claim 9, wherein the amount of the carbonyl compound of formula (2) used is from 5 to 300 mol per mol of the fluoral equivalent represented by formula (1).

11. The process according to claim 1, wherein the optically active amino acid or derivative thereof is selected from the group consisting of alanine, cysteine, serine, threonine, methionine, valine, leucine, isoleucine, asparagine, glutamine, 2-azetidinecarboxylic acid, proline, phenylglycine, phenylalanine, tylosine, tryptophan, aspartic acid, glutamic acid, lysine, arginine, histidine, ornithine, citrulline, creatine, phosphoserine, γ-carboxyglutamic acid, cis- or trans-4-hydroxyproline, cis- or trans-4-acetoxyproline, cis- or trans-4-t-butoxyproline, pipecolic acid, indoline-2-carboxylic acid, 2-methoxymethylpyrrolidine, and an optically active amino acid derivative represented by formula (8):

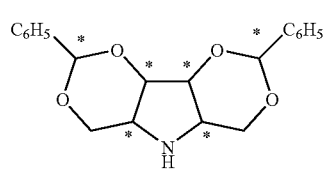
(8)

wherein the symbol * represents an asymmetric carbon and each independently has R configuration or S configuration.

12. The process according to claim 11, wherein the optically active amino acid is proline, cis- or trans-4-hydroxyproline, phenylglycine, indoline-2-carboxylic acid, or 2-methoxymethylpyrrolidine.

13. The process according to claim 12, wherein the optically active amino acid is R(d)- or S(l)-proline.

14. The process according to claim 1, wherein the optically active amino acid is used in an amount of from 0.01 to 3 mol per mol of the fluoral equivalent represented by formula (1).

15. The process according to claim 13,
wherein the fluoral equivalent of formula (1) is represented by formula (5):

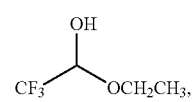
(5)

wherein the carbonyl compound of formula (2) is represented by formula (6):

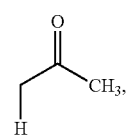
(6)

and
wherein the optically active β-trifluoromethyl-β-hydroxy-carbonyl compound of formula (3) is represented by formula (7):

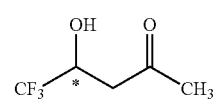
(7)

wherein the symbol * represents an asymmetric carbon.

16. The process according to claim 1, wherein the reaction temperature is from −50 to +150° C.

17. The process according to claim 1, wherein the reaction time is from 0.1 to 240 hours.

18. The process according to claim 1, further comprising a step of purifying the reaction product.

19. The process according to claim 1, further comprising a step of recovering the optically active amino acid or derivative thereof.

20. The process according to claim 19, wherein the recovering step comprises filtration.

* * * * *